United States Patent

Arrang et al.

Patent Number: 5,290,790
Date of Patent: Mar. 1, 1994

[54] 4-(4-IMIDAZOLYL) PIPERIDINES SUBSTITUTED AT POSITION 1, THEIR PREPARATION AND ALSO THEIR THERAPEUTIC APPLICATIONS

[75] Inventors: Jean-Michel Arrang, Gif/Yvette; Monigue Garborg, Paris; Jean-Charles M. Lancelot, Tour en Bessin; Jeanne-Marie Lecomte, Paris; Max-Fernand Robba, Caen; Jean-Charles Schwartz, Paris, all of France

[73] Assignees: National De La Sante et De La Recherche Medicale; Societe Civile Bioprojet, both of Paris; Universite De Caen - Esplanade De La Faix, Caen Cedex, all of France

[21] Appl. No.: 814,450

[22] Filed: Dec. 30, 1991

[30] Foreign Application Priority Data

Dec. 31, 1990 [FR] France .................. 90 16540

[51] Int. Cl.$^5$ .................. A61K 31/445; C07D 401/04; C07D 405/14
[52] U.S. Cl. .................. 514/326; 514/316; 546/186; 546/187; 546/208; 546/209; 546/210
[58] Field of Search .............. 546/210, 208, 209, 186, 546/187; 514/326, 316

[56] References Cited

U.S. PATENT DOCUMENTS

| | | | |
|---|---|---|---|
| 4,431,653 | 2/1984 | Wei et al. | 546/210 |
| 4,675,403 | 6/1987 | Abou-Gharbia | 546/210 |
| 4,707,487 | 11/1987 | Arrang et al. | 546/210 |
| 5,059,601 | 10/1991 | Salimbeni | 546/210 |

FOREIGN PATENT DOCUMENTS

0197840 10/1986 European Pat. Off.

OTHER PUBLICATIONS

*Chemical Abstracts*, vol. 80, No. 15, p. 389, No. 82801a (1985).

Primary Examiner—C. Warren Ivy
Assistant Examiner—Celia Chang
Attorney, Agent, or Firm—Larson and Taylor

[57] ABSTRACT

The compounds correspond to the general formula

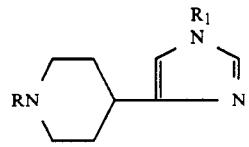

in which $R_1$ represents a hydrogen atom or a group $-COR_2$, in which $R_2$ represents a benzene ring, cyclopentylmethyl, cyclohexylmethyl, cyclopentylethyl or cyclohexylethyl groups or cyclopentylamine, cyclohexylamine or phenylamine, chlorophenylamine or dichlorophenylamine groups; R represents a hydrogen atom or a group $COR_3$, in which $R_3$ represents an aliphatic group, a cyclane or benzene ring-system, a group a group $(CH_2)^m R_4$, a group $-CH=CHR_8$ or a secondary amine group $-NH(CH_2)_n R_g$; R also represents a hydroxyalkenyl group:

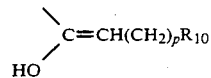

3 Claims, No Drawings

4-(4-IMIDAZOLYL) PIPERIDINES SUBSTITUTED AT POSITION 1, THEIR PREPARATION AND ALSO THEIR THERAPEUTIC APPLICATIONS

The present invention relates to new 4-(4-imidazolyl)-piperidines substituted at position 1, to their preparation and also to their therapeutic applications.

The compounds according to the invention correspond to the general formula

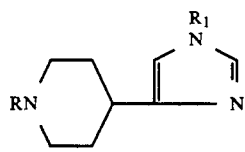   I in which $R_1$ represents a hydrogen atom or a group —$COR_2$, in which $R_2$ represents a benzene ring, cyclopentylmethyl, cyclohexylmethyl, cyclopentylethyl or cyclohexylethyl groups or cyclopentylamine, cyclohexylamine or phenylamine, chlorophenylamine or dichlorophenylamine groups; R represents a hydrogen atom or a group $COR_3$, in which $R_3$ represents (a) a linear or branched aliphatic group containing 1 to 11, and in particular 1 to 9, carbon atoms, (b) a cyclane ring-system such as cyclopropane, phenylcyclopropane, cyclobutane, cyclopentane, cyclohexane, cycloheptane, norbornane, adamantane, noradamantane, chlorooxonorbornane, chloroethylenedioxynorbornane, bromoethylenedioxynorbornane and the anhydride group of hydroxycarboxy-1,2,2-trimethylcyclopentanecarboxylic acid, (c) a benzene ring, unsubstituted or substituted at the para-position with a linear or branched aliphatic group containing 3 to 5 carbon atoms, as well as with a halogen, (d) a group $(CH_2)^m R_4$, in which m is a number between 1 and 10, and $R_4$ represents a cyclane ring system such as cyclopropane, cyclobutane, cyclopentane, cyclopentene, cyclohexane, cycloheptane, norbornane, noradamantane, adamantane and 6,6-dimethylbicyclo[3.1.1]heptene; a benzene ring, unsubstituted or monosubstituted with a fluorine atom, a chlorine atom, a methyl group or a methoxy group; a thiophene ring grafted via its ring-position 2 or its ring-position 3; a carboxylic acid ester group $COOR_5$, in which $R_5$ is a cyclane ring-system such as cyclopropane, cyclobutane, cyclopentane, cyclohexane or norbornane; a carboxylic acid amide group of structure $CONHR_6$, in which $R_6$ represents a cyclane ring-system such as cyclopropane, cyclobutane, cyclopentane, cyclohexane or norbornane; a carboxylic acid amide group of structure

in which the group

represents pyrrolidine, piperidine or 2,6-dimethylmorpholine; or an ether group —O—$R_7$, it being possible for $R_7$ to be a benzene ring, unsubstituted or monosubstituted with a chlorine or fluorine atom or disubstituted with a chlorine atom and with a methyl group;

(e) a group —CH=$CHR_8$, in which $R_8$ represents a cyclane ring-system such as cyclopropane, cyclobutane, cyclopentane, cyclohexane, norbornane or norbornene;

(f) a secondary amine group —$NH(CH_2)_n R_9$, in which n is a number between 1 and 5 and $R_9$ constitutes a cyclane ring-system such as cyclopropane, cyclobutane, cyclopentane, cyclohexane or norbornane, or a benzene ring, unsubstituted, monosubstituted with a fluorine or chlorine atom or with a methoxy group or trisubstituted with methoxy groups;

R also represents a hydroxyalkenyl group

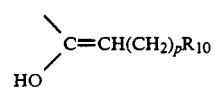

in which p is a number between 2 and 9 and $R_{10}$, represents a benzene ring or a phenoxy group; as well as a group

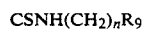

in which n is a number between 1 and 5 and $R_9$ has the meaning stated above.

The compounds of formula I according to the invention in which $R_1$ denotes hydrogen and R has the meaning stated above are prepared by the reaction of 4-(4-imidazolyl)piperidine of formula

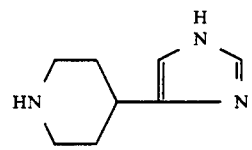   II a) with an acid chloride $R_3COCl$ or a mixed anhydride such as $R_3CO_2CO_2C_2H_5$ when it is desired to obtain amides of general formula

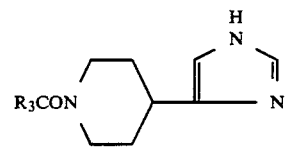   III or b) when it is desired to prepare ureas of formula IV or thioureas of formula V

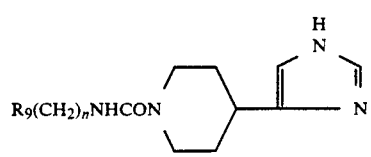   IV

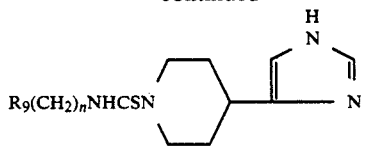

where n and $R_9$ have the meaning stated above, with an isocyanate $R_9(CH_2)_nNCO$, obtained from an acid $R_9(CH_2)_nCOOH$ by a modification of the Curtius synthesis, or with an isothiocyanate $R_9(CH_2)_nNCS$.

The compounds of formula I according to the invention in which $R_1$ denotes a group $COR_2$ and R has the meaning stated above are obtained by the reaction of a compound of formula

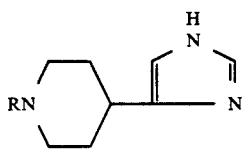

where R has the meaning stated above, a) with an acid chloride $R_2COCl$ when it is desired to obtain a compound of formula

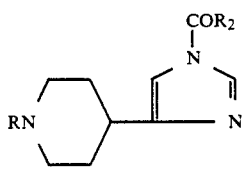

where $R_2$ represents a benzene ring or cyclopentylmethyl, cyclohexylmethyl, cyclopentylethyl or cyclohexylethyl groups; or b) with the corresponding isocyanate when it is desired to obtain a compound of formula VII where $R_2$ represents cyclopentylamine, cyclohexylamine, phenylamine, chlorophenylamine or dichlorophenylamine groups.

The reaction set out under a) is performed, for example, by heating to a temperature of the order of 80° C. in acetonitrile in the presence of triethylamine.

The condensation reaction with the isocyanate or isothiocyanate set out under b) is performed in a manner known per se, under reflux in an apolar solvent such as benzene.

The compounds according to the invention corresponding to the general formula I may be salified with the inorganic acids or organic acids which are commonly used for therapeutic purposes in salt form.

The examples which are given below without implied limitation illustrate the present invention.

Examples 1 to 7 illustrate the preparation of the compounds of general formula I in which R has the meaning stated above and $R_1$ represents hydrogen.

Examples 8 and 9 describe the general methods of synthesis of the isocyanates and the N-(4-imidazolyl)-piperidylureas (compounds of formula IV).

Example 10 illustrates the preparation of a thiourea of formula V.

Examples 11 and 12 illustrate the preparation of the compounds of general formula I in which R has the meaning stated above and R, represents a group $COR_2$, $R_2$ having the meaning stated above.

EXAMPLE 1

1-(Norbornylmethylcarbonyl)-4-(1H-imidazol-4-yl)piperidine (Compound 23)

2.03 g (0.0132 mol) of triethylamine are added dropwise at 0° C. to a solution of 2 g (0.0132 mol) of 2-norbornaneacetic acid in 60 ml of acetonitrile. After 30 minutes' stirring, 1.43 g (0.0132 mol) of ethyl chloroformate are added dropwise in such a way that the temperature remains between 0° C. and 5° C. After 30 minutes' stirring, the solution is poured into 60 ml of acetonitrile and 15 ml of water containing 1.99 g (0.0132 mol) of 4-(4-imidazolyl)piperidine. The reaction mixture is heated to 80° C. for 1 hour. After cooling, the solution is concentrated under reduced pressure. The oily residue is taken up in 40 ml of water and then extracted with an ethyl ether/ethyl acetate (60:40) mixture. The organic phase is dried over magnesium sulphate, filtered and then concentrated under reduced pressure. The residual oil crystallises on adding an ethyl ether/petroleum ether/hexane (20:5:5) mixture. After recrystallisation in an ether/petroleum ether (60:40) mixture, a white powder is obtained.

M.p. 118°–120° C.

Mass = 2.2 g

Yield = 58% IR spectrum (KBr); main bands; 3120 (NH), 1635 (C=O), 1450, 1310, 1275, 1205, 1030, 990, 870, 770 and 645 cm$^{-1}$.

Analysis: $C_{17}H_{25}N_3O$:

Calc %: C: 71.04 H : 8.77 N : 14.62. Found %: C: 71.19 H : 8.63 N : 14.79.

$^1$H NMR spectrum (DMSO-d$_6$): imidazole H2 : 7.50 ppm; imidazole H5 : 6.71 ppm; piperidine and norbornyl H: 4.33, 3.90, 3.43, 2.76, 2.00, 1.26 ppm (in the form of unresolved peaks).

Compounds 1 to 22, 24 to 58 and 62 to 66 (Table I) are obtained in a similar manner to Compound 23.

EXAMPLE 2

1-(Norbornylpropionylcarbonyl)-4-(1H-imidazol-4-yl)piperidine (Compound 24)

A. 3-(2-Norbornyl)propionic Acid

A solution of 20 g (0.129 mol) of 2-norbornylacetic acid and 3 equivalents of lithium aluminium hydride in 300 ml of anhydrous ether is brought to reflux for 4 hours. After hydrolysis of the solution and when settling has taken place, the ether phase is separated, washed with water, dried and then concentrated under reduced pressure. 14 g (77%) of 2-(2-hydroxymethyl)-norbornane are obtained. These 14 g (0.1 mol) of alcohol are dissolved in 60 ml of pyridine at 0° C., and 38.10 g (2 equivalents) of tosyl chloride are added in small portions. The mixture is stirred for 8 h at room temperature. The solution is hydrolysed with 250 ml of ethyl ether. The ether phase is separated after settling has taken place, dried and concentrated under reduced pressure. The residual oil (mass = 23 g, yield = 78%) is dissolved in 50 ml of DMSO in the presence of 10 g (0.153 mol) of potassium cyanide and brought to 80° C. for 2 h. After extraction of the solution with 500 ml of ethyl ether, 7 g (60%) of 3-(2-norbornyl)propionitrile are obtained.

The 7 g (0.046 mol) of nitrile are heated to reflux in 70 ml of 20% aqueous sodium hydroxide solution. After cooling, the solution is extracted with 70 ml of ether. After separation when settling has taken place, the aqueous phase is acidified with concentrated hydrochloric acid solution. After extraction with 170 ml of ether, 5 g (64%) of 3-(2-norbornyl)propionic acid are obtained in the form of a pale yellow oil.

B.p. 150° C./5 mm

IR spectrum (KBr):(CO) 1700, main bands at 1410, 1280, 1220 and 930 cm⁻

Analysis: $C_{10}H_{15}O_2$: Calculated %: C: 71.39 H : 9.58. Found %: C: 71.42 H : 9.60.

B.
1-(Norbornylpropionylcarbonyl)-4-(1H-imidazol-4-yl)piperidine 2.03 g (0.0132 mol) of triethylamine are added dropwise at 0° C. to a solution of 2.21 g (0.0132 mol) of the compound obtained under A in 70 ml of acetonitrile. After 30 minutes' stirring, 1.43 g (0.0132 mol) of ethyl chloroformate are added in such a way that the temperature remains between 0° C. and 5° C. After 30 minutes' stirring, the solution is poured into 60 ml of acetonitrile and 15 ml of water containing 1.99 g (0.0132 mol) of 4-(4-imidazolyl)piperidine. After being heated to 80° C. for 1 hour, the solution is concentrated under reduced pressure and the oily residue is taken up with 20 ml of water and then extracted with 70 ml of ethyl acetate. The residual oil obtained crystallises on adding an ethyl ether/petroleum ether (30:20) mixture. After recrystallisation in an ethyl acetate/ether (30:20) mixture, the compound of the title is obtained in the form of a white powder.

M.p. 158° C.
Mass=2.6 g
Yield=65%
IR spectrum (KBr): (NH) 3130, (CO) 1640 cm⁻¹.
Analysis: C, H, N.

EXAMPLE 3

1-(1-Hydroxy-4-phenyl-1-buten-1-yl)-4-(4-imidazolyl)-piperidine (Dihydrochloride) (Compound 59)

2.03 g (0.0132 mol) of triethylamine are added dropwise at 0° C. to a solution of 2.16 g (0.0132 mol) of 4-phenylbutyric acid in 70 ml of acetonitrile. After 30 minutes' stirring, 1.43 g (0.0132 mol) of ethyl chloroformate are added in such a way that the temperature remains between 0° C. and 5° C. After 30 minutes, stirring, the solution is poured into 60 ml of acetonitrile and 15 ml of water containing 1.99 g (0.0132 mol) of 4-(4-imidazolyl)piperidine. After being heated to 80° C. for 1 hour, the solution is concentrated under reduced pressure and the oily residue is taken up with 20 ml of water and then extracted with 70 ml of ethyl acetate. The residual oil obtained crystallises on adding an ethyl ether/petroleum ether (30:20) mixture. After recrystallisation in an ether/hexane (30:20) mixture a white powder (Compound 42) is obtained.

M.p. 102° C.
Mass=3.2 g
Yield=81%

3.2 g (0.81 mol) of the base obtained (Compound 42) are then added to 20 ml of isopropanol in the presence of 2.1 equivalents of concentrated hydrochloric acid. The precipitate is drained and washed with 10 ml of isopropyl alcohol and then with 15 ml of ethyl ether. After drying, the precipitate is recrystallised in acetonitrile. The compound of the title is obtained in the form of a white powder.

M.p. 126° C.
Yield=55%
Analysis: C, H, N, Cl. Recrystallisation in acetonitrile (70)+ethyl ether (30).

EXAMPLE 4

1-(1-Hydroxy-11-phenoxy-1-undecen-1-yl)-4-(4-imidazolyl)piperidine (dihydrochloride) (Compound 60)

This compound is obtained according to the same synthesis process as compound 59 of Example 3, starting with the base 58 (Table I).

M.p. 115° C.
Yield=55%
Analysis: C, H, N, Cl. Recrystallisation in acetonitrile (7)+ethyl ether (3).

EXAMPLE 5

1-(3-Phenylpropionyl)-4-(1H-imidazol-4-yl)piperidine (Oxalate) (Compound 38)

0.5 (0.0017 mol) of 1-(3-phenylpropionyl)-4-(1H-imidazol-4-yl)piperidine and 1.2 equivalents of oxalic acid dissolved in 35 ml of isopropanol are brought to reflux for 1 h. After cooling, the precipitate obtained is drained,,washed with ethyl ether, dried and recrystallised in acetonitrile. A white powder is obtained.

M.p. 129° C.
Mass=0.59 g
Yield=94%
Analysis (C, H, N).

EXAMPLE 6

1-(Cyclohexylaminocarbonyl-n-pentanoyl)-4-(1H-imidazol-4-yl)piperidine (Compound 54)

A. Adipic acid mono-N-cyclohexylamide 34.8 g (0.2 mol) of adipic acid monoethyl ester are added dropwise and with stirring to 19.8 g (0.2 mol) of cyclohexylamine. The temperature rises to 60° C. The reaction mixture is heated to 80° C. for 1 h. After cooling, the solution is poured into 200 ml of water and then extracted with 300 ml of ethyl ether. The ether phase is stirred into 150 ml of potassium hydrogen carbonate solution. After separation of the ether phase when settling has taken place, the aqueous phase is acidified to pH 1 with concentrated hydrochloric acid. The precipitate is drained, washed with water, dried and recrystallised in acetonitrile.

Mass=31 g
M.p. 154° C.
Yield=68%

B.
1-(Cyclohexylaminocarbonyl-n-pentanoyl)-4-(1H-imidazol-4-yl)piperidine

The compound obtained under A yields the compound of the title by applying the same process as that described in Example 2.B.

EXAMPLE 7

1-(Cyclopentenylmethylcarbonyl)-4-(1H-imidazol-4-yl)piperidine (Compound 61)

2.03 g (0.0132 mol) of triethylamine are added dropwise at 0° C. to a solution of 1.66 g (0.0132 mol) of cyclopenteneacetic acid in 70 ml of acetonitrile. After 30 minutes' stirring, 1.43 g (0.0132 mol) of ethyl chloroformate are added in such a way that the temperature remains between 0° C. and 5° C. After 30 minutes' stirring, the solution is poured into 60 ml of acetonitrile and 15 ml of water containing 1.99 g (0.0132 mol) of 4-(4-imidazolyl)piperidine. After being heated to 80° C. for 1 hour, the solution is concentrated under reduced pressure and the oily residue is taken up in 200 ml of water and then extracted with 70 ml of ethyl acetate. The residual oil obtained crystallises on adding an ethyl ether/petroleum ether (3:2) mixture. The compound of the title is obtained in the form of a white powder (recrystallisation in ether/petroleum ether (60:40)).

M.p. 107° C.
Mass=2 g
Yield=58%
IR spectrum (KBr): 3130 (NH), 1640 (CO) cm$^{-1}$
Analysis: C, H, N.

EXAMPLE 8

General Method of Synthesis of the Isocyanates (Compounds 67 to 75)

(x mol) of triethylamine are added to (x mol) of acid dissolved in x ml of acetonitrile at 0° C.; after 30 min of contact, (x mol) of ethyl chloroformate is/are added dropwise and the mixture is left stirring at this temperature for 40 min. (x mol) of sodium azide in (x ml) of water are added dropwise in the course of 10 min to the above solution. After 1h of contact, the precipitate is drained and the filtered solution is hydrolysed with 200 ml of cold water and then extracted with 200 ml of ethyl ether. The ether phase is dried over magnesium sulphate and calcium chloride. After evaporation under vacuum at 40° C., the residual oil is taken up with 60 ml of benzene and brought to reflux for 2 h. The benzene solution is washed with water, separated after settling has taken place, dried and then concentrated under reduced pressure. The residual oil is distilled under a pressure of 5 mm. The isocyanates obtained (Table II) take the form of oils which are stored under nitrogen and protected from light, since they form symmetrical ureas very rapidly.

EXAMPLE 9

General Method of Synthesis of the N-(4-Imidazolyl)piperidylureas (oxalates) (Compounds 76 to 84 in Table III)

A solution of 2.5 g (0.016 mol) of isocyanate and 2.41 g (0.016 mol) of 4-(4-imidazolyl)piperidine in 60 ml of benzene is heated to reflux for 1h 30 min. After cooling of the solution and when settling has taken place, the benzene is separated and the residual oil is taken up in 60 ml of acetone, stirred at 40° C. and then treated with a slight excess of oxalic acid. The mixture is heated to boiling for 35 min. After cooling, the precipitate formed is drained, washed with ethyl ether, dried and recrystallised.

The ureas 76 to 84 described in TABLE III are synthesised in a similar manner.

EXAMPLE 10

4-(1-Phenethylaminocarbothioyl-4-piperidyl)-1H-imidazole (oxalate) (Compound 85)

A solution of 1.63 g (0.01 mol) of phenethyl isothiocyanate in 60 ml of toluene and 1.51 g (0.01 mol) of 4-(4-imidazolyl)piperidine is heated to reflux for 1h 30 min. After cooling, the solution is evaporated under reduced pressure and the residual oil obtained is dissolved in 60 ml of isopropanol in the presence of 1.2 equivalents of oxalic acid. After 30 minutes of heating at 80° C., the white precipitate formed is drained, washed with ether and recrystallised in acetonitrile.

M.p. 201° C.
Mass=2.7 g
Yield=67%
Analysis: $C_{19}H_{24}H_4O_4S$: Calculated %: C : 56.43 ; H : 5.90 ; N : 13.86. Found %: C : 56.55 ; H : 5.91 ; N : 13.90.

EXAMPLE 11

1-(3-Cyclopentylpropionyl)-4-[1-(3-cyclopentylpropionyl)-4-Imidazolyl]piperidine (Compound 86)

1 g (0.0036 mol) of 1-(3-cyclopentylpropionyl)-4-(1H-imidazol-4-yl)piperidine and 0.57 9 (0.0036 mol) of 3-cyclopentylpropionyl chloride in 70 ml of toluene are brought to reflux for 1h in the presence of 2 ml of triethylamine. After cooling, the solution is evaporated under reduced pressure and the residue is taken up with 100 ml of water and then extracted with 200 ml of ethyl ether. The compound of the title is obtained in the form of a white powder (recrystallisation in acetone).

Mass=0.71 g
Yield=50%
IR spectrum (KBr): (CO) 1620, 1650 cm$^{-1}$
Analysis: $C_{24}H_{37}N_3O_2$:
Calculated %: C : 72.15 H : 9.30 N : 10.51. Found %: C : 72.47 H : 9.23 N : 10.97.

Compounds 87 and 88 (Table V) are obtained in a similar manner.

EXAMPLE 12

1-(4-Phenoxybutylryl)-4-[1-(2,4-Dichlorophenylaminocarbonyl)-4-imidazolyl]piperidine (Compound 92)

1 g (0.00319 mol) of 1-(4-phenoxybutyryl)-4-(1H-imidazol-4-yl)piperidine and 0.59 g (0.00319 mol) of 2,4-dichlorophenyl isocyanate in 50 ml of toluene are brought to reflux for 2h. The precipitate formed is drained and washed with ethyl ether. The compound of the title is obtained in the form of a white powder (recrystallisation in ethyl acetate).

M.p. 124° C.
Mass=0.51 g
Yield=30%
IR spectrum (KBr): (CO) 1625 and 1640 cm$^{-1}$
Analysis: $C_{25}H_{25}N_4Cl_2$: Calculated %: C : 58.94 ; H : 5.14 N : 10.99 Cl :13.91. Found %: C : 58.96 ; H: 5.20 ; N: 10.87 ; Cl : 14.00.

Compounds 89, 90, 91, 93 and 94 (Table V) are obtained in a similar manner.

The compounds of the above Examples are collated in the following Tables I to V.

TABLE I

Structure: RN-piperidine-C(=CH-NH-CH=N.HX) (imidazole-type ring shown)

| Comp. No | R | HX | M.p. (°C.) | Yld (%) | Analysis | Recrystallisation solvent |
|---|---|---|---|---|---|---|
| 1 | $CH_3(CH_2)_5-CO-$ | $(CO_2H)_2$ | 86 | 29 | C,H,N | Ethyl acetate (3) Ether (2) |
| 2 | cyclopropyl-CO- | | 160 | 76 | C,H,N | Ethyl acetate |
| 3 | cyclobutyl-CO- | | 153 | 53 | C,H,N | Ethyl acetate |
| 4 | cyclopentyl-CO- | | 165 | 86 | C,H,N | Ethyl acetate |
| 5 | cyclohexyl-CO- | | 106 | 71 | C,H,N | Ethyl ether |
| 6 | cycloheptyl-CO- | $(CO_2H)_2$ | 100 | 60 | C,H,N | Ethyl ether |
| 7 | norbornyl-CO- | | 158 | 50 | C,H,N | Ethyl acetate (3) Ether (2) |
| 8 | adamantyl-CO- | $(CO_2H)_2$ | 108 | 57 | C,H,N | Isopropanol |
| 9 | adamantyl-CO- | $(CO_2H)_2$ | 167 | 55 | C,H,N | Isopropanol |
| 10 | Cl-substituted bicyclic ketone-CO- | $(CO_2H)_2$ | 168 | 45 | C,H,N | Ethyl acetate (3) Ether (2) |
| 11 | camphor-derived -CO- ($H_3C$, $CH_3$, $CH_3$) | | 164 | 40 | C,H,N | Ethyl acetate (3) Ether (2) |

TABLE I-continued

[Structure: RN-piperidine connected to imidazole ring with N.HX, containing H-N]

| Comp. No | R | HX | M.p. (°C.) | Yld (%) | Analysis | Recrystallisation solvent |
|---|---|---|---|---|---|---|
| 12 | methylcyclopropyl-CO— (CH₃ on cyclopropyl) | | 126 | 60 | C,H,N | Acetone (4) Ether (1) |
| 13 | phenylcyclopropyl-CO— | | 144 | 60 | C,H,N | Ethyl acetate (3) Ether (2) |
| 14 | phenyl-CO— | | 150 | 65 | C,H,N | Acetone (4) Ether (1) |
| 15 | 4-F-phenyl-CO— | (CO₂H)₂ | 158 | 40 | C,H,N,F | Acetone (3) Ether (2) |
| 16 | 4-I-phenyl-CO— | | 198 | 55 | C,H,N,I | Ethyl acetate (3) Ether (2) |
| 17 | 4-CH₃(CH₂)₃-phenyl-CO— | | 151 | 70 | C,H,N | Acetonitrile (3) Ether (2) |
| 18 | 4-(CH₃)₃C-phenyl-CO— | | 174 | 80 | C,H,N | Ethyl acetate (3) Ether (1) |
| 19 | cyclopropyl-CH₂CO— | (CO₂H)₂ | 115 | 20 | C,H,N | Ethyl acetate (3) Ether (2) |
| 20 | cyclobutyl-CH₂CO— | | 128 | 60 | C,H,N | ethyl ether |
| 21 | cyclopentyl-CH₂CO— | | 122 | 41 | C,H,N | Ethyl ether |
| 22 | cyclohexyl(H)-CH₂CO— | | 164 | 70 | C,H,N | Acetonitrile |
| 23 | norbornyl-CH₂CO— | | 118–120 | 60 | C,H,N | Ethyl ether |

TABLE I-continued

[Structure: RN-piperidine-C(=CH-NH)-CH=N·HX (imidazole-type)]

| Comp. No | R | HX | M.p. (°C.) | Yld (%) | Analysis | Recrystallisation solvent |
|---|---|---|---|---|---|---|
| 24 | [bicyclo[2.2.2]octyl]-CH₂CH₂CO— | | 158 | 65 | C,H,N | Ethyl acetate (3) Ether (2) |
| 25 | [adamantyl]-CH₂CO— | | 118 | 55 | C,H,N | Acetone |
| 26 | [3-methyladamantyl]-CH₂CO— | | 134 | 30 | C,H,N | Ethyl ether |
| 27 | [phenyl]-CH₂CO— | | 188 | 45 | C,H,N | Ether (1) Ethyl acetate (2) |
| 28 | [4-chlorophenyl]-CH₂CO— | | 157 | 20 | C,H,N | Ether (1) Ethyl acetate (1) Petroleum ether (1) |
| 29 | [thien-3-yl]-CH₂CO— | | 142 | 30 | C,H,N,S | Ethyl ether |
| 30 | [cyclopropyl]-CH₂CH₂CO— | | 109 | 10 | C,H,N | Ethyl acetate (3) Ether (2) |
| 31 | [cyclobutyl]-CH₂CH₂CO— | | 124 | 10 | C,H,N | Ethyl acetate (2) Ether (2) |
| 32 | [cyclopentyl]-CH₂CH₂CO— | | 116 | 73 | C,H,N | Ethyl ether |
| 33 | [cyclohexyl]-CH₂CH₂CO— | | 110 | 68 | C,H,N | Ethyl ether |
| 34 | [norbornyl]-CH₂CH₂CO— | | 158 | 65 | C,H,N | Ethyl acetate |

TABLE I-continued

[Structure: RN-piperidine-4-yl substituted with imidazole-N.HX group]

| Comp. No | R | HX | M.p. (°C.) | Yld (%) | Analysis | Recrystallisation solvent |
|---|---|---|---|---|---|---|
| 35 | 1-adamantyl-CH$_2$CH$_2$CO— | | 134 | 30 | C,H,N | Acetone |
| 36 | cubyl-CH$_2$CH$_2$CO— | | 100 | 15 | C,H,N | Ethyl ether |
| 37 | phenyl-CH$_2$CH$_2$CO— | | 121 | 40 | C,H,N | Ether (1), Ethyl acetate (2) |
| 38 | phenyl-CH$_2$CH$_2$CO— | (CO$_2$H)$_2$ | 129 | 94 | C,H,N | Acetonitrile |
| 39 | 4-CH$_3$O-phenyl-CH$_2$CH$_2$CO— | | 123 | 63 | C,H,N | Ether (1) Petroleum ether (1) |
| 40 | cyclopentyl-(CH$_2$)$_3$CO— | | 144 | 60 | C,H,N | Ether (1) Petroleum ether (1) |
| 41 | cyclohexyl-(CH$_2$)$_3$CO— | | 146 | 60 | C,H,N | Ethyl acetate |
| 42 | phenyl-(CH$_2$)$_3$CO— | | 102 | 81 | C,H,N | Ether (3) Hexane (2) |
| 43 | 2-thienyl-(CH$_2$)$_3$CO— | | 103 | 70 | C,H,N,S | Ethyl ether |
| 44 | phenyl-(CH$_2$)$_4$CO— | | 103–105 | 65 | C,H,N | Ethyl ether |
| 45 | CH$_3$(CH$_2$)$_6$CO— | | 100 | 45 | C,H,N | Ethyl ether (4) Petroleum ether (1) |
| 46 | CH$_3$(CH$_2$)$_8$CO— | | 95 | 55 | C,H,N | Ethyl ether (4) Petroleum ether (1) |

TABLE I-continued

[Structure: RN-piperidine-4-yl attached to vinyl-imidazole, with N.HX]

| Comp. No | R | HX | M.p. (°C.) | Yld (%) | Analysis | Recrystallisation solvent |
|---|---|---|---|---|---|---|
| 47 | Ph(CH$_2$)$_5$CO— | | 102 | 56 | C,H,N | Ether (3) Hexane (2) |
| 48 | Ph(CH$_2$)$_6$CO— | | 92 | 65 | C,H,N | Ether (3), Hexane (1) Petroleum ether (1) |
| 49 | Ph(CH$_2$)$_7$CO— | | 120 | 75 | C,H,N | Ethyl ether |
| 50 | norbornenyl-CH=CHCO— | (CO$_2$H)$_2$ | 136 | 45 | C,H,N | Isopropanol |
| 51 | norbornyl-CO$_2$(CH$_2$)$_2$CO— | | 189 | 70 | C,H,N | Ether (1), Ethyl acetate (4) |
| 52 | cyclopentyl-NHCO(CH$_2$)$_2$CO— | | 175 | 20 | C,H,N | Acetone |
| 53 | norbornyl-NHCO(CH$_2$)$_2$CO— | | 124 | 40 | C,H,N | Ethyl acetate (3) Ether (2) |
| 54 | cyclohexyl-NHCO(CH$_2$)$_4$CO— | | 121 | 35 | C,H,N | ethyl ether |
| 55 | (iPr)$_2$N(CH$_2$)$_4$CO— (morpholine-like with 2 CH$_3$) | | 122 | 20 | C,H,N | Acetone (4) Ether (1) |
| 56 | PhO(CH$_2$)$_3$CO— | | 115 | 43 | C,H,N | Ethyl ether |
| 57 | (4-Cl-2-CH$_3$-phenyl)O(CH$_2$)$_3$CO— | | 155 | 60 | C,H,N | Acetonitrile |

TABLE I-continued

Structure:
```
       H
       N
      ╱ ╲
RN—[piperidine]—C=CH
              ╲
               N.HX
```

| Comp. No | R | HX | M.p. (°C.) | Yld (%) | Analysis | Recrystallisation solvent |
|---|---|---|---|---|---|---|
| 58 | C₆H₅—O(CH₂)₁₀CO— (phenoxy) |  | 103 | 45 | C,H,N | Ethyl ether |
| 59 | (CH₃)(HO)C=CH—(CH₂)₂—C₆H₅ | HCl | 126 | 55 | C,H,N,Cl | Acetonitrile (7) Ethyl ether (3) |
| 60 | (CH₃)(HO)C=CH—(CH₂)₉—OC₆H₅ | HCl | 115 | 55 | C,H,N,Cl | Acetonitrile (7) Ethyl ether (3) |
| 61 | cyclopentenyl-CH₂CO— |  | 107 | 58 | C,H,N | Ether (6) Petroleum ether (4) |
| 65 | —CO(CH₂)₁₀—CH₃ |  | 94 | 22 | C.H,N | Ether ether hexane 1:1 |
| 64 | —CO(CH₂)₉—CH₃ |  | 114 | 48 | C,H,N | Ethyl ether |
| 62 | —CO(CH₂)₄CH₃ |  | 104 | 61 | C,H,N | Ethyl ether |
| 63 | —CO(CH₂)₇CH₃ |  | 36 | 52 | C,H,N | Ethyl ether/ hexane 1:1 |
| 66 | —CO—C₆H₄—Cl (para) | (CO₂H)₂ | 118 | 73 | C,H,N | Ethyl ether/ethyl acetate 1:4 |

TABLE II

R₉(CH₂)ₙNCO

| Comp. No | R₉ | n | B.p. (5 mm) (°C.) | IR (NCO) | Yld % | Analyses |
|---|---|---|---|---|---|---|
| 67 | cyclopentyl | 2 | 150 | 2190 | 20 | C,H,N |
| 68 | cyclohexyl (H) | 2 | 170 | 2180 | 25 | C,H,N |
| 69 | cyclohexyl (H) | 3 | 185 | 2180 | 30 | C,H,N |
| 70 | norbornyl | 1 | 190 | 2190 | 40 | C,H,N |

TABLE II-continued
R$_9$(CH$_2$)$_n$NCO
| Comp. No | R$_9$ | n | B.p. (5 mm) (°C.) | IR (NCO) | Yld % | Analyses |
|---|---|---|---|---|---|---|
| 71 | 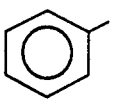 | 2 | 180 | 2185 | 20 | C,H,N |
| 72 | 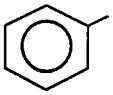 | 3 | 190 | 2180 | 20 | C,H,N |
| 73 | 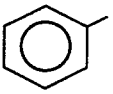 | 4 | 195 | 2180 | 25 | C,H,N |
| 74 | 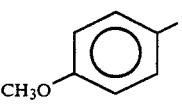 | 2 | 185 | 2190 | 20 | C,H,N |
| 75 | 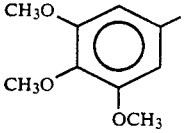 | 2 | 210 | 2190 | 20 | C,H,N |
TABLE III
| Comp. No | R$_9$ | n | M.p. (°C.) | Yld % | Recrystallisation solvent |
|---|---|---|---|---|---|
| 76 | 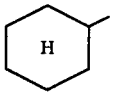 | 2 | 148 | 30 | Isopropanol |
| 77 | 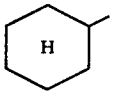 | 2 | 120 | 20 | Isopropanol |
| 78 |  | 3 | 130 | 20 | Isopropanol |
| 79 | 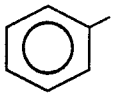 | 1 | 102 | 60 | Isopropanol |
| 80 | 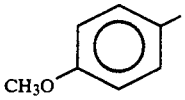 | 2 | 136 | 15 | Isopropanol: (6) Ethyl ether: (4) |
| 81 | 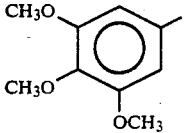 | 2 | 130 | 20 | Isopropanol: (3) Ethyl ether: (3) Hexane: (4) |
| 82 | 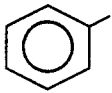 | 2 | 92 | 15 | Isopropanol: (6) Ethyl ether: (4) |
| 83 | 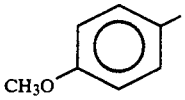 | 3 | 136 | 15 | Isopropanol (6) Ethyl ether (4) |

TABLE III-continued

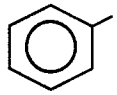

CONH(CH₂)ₙR₉

| Comp. No | R₉ | n | M.p. (°C.) | Yld % | Recrystallisation solvent |
|---|---|---|---|---|---|
| 84 | 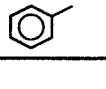 | 4 | 158 | 15 | Isopropanol |

TABLE IV

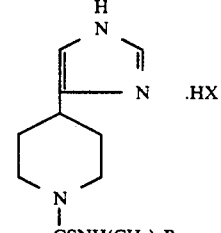 .HX

CSNH(CH₂)ₙR₉

| Comp. No | R₉ | n | HX | M.p. (°C.) | Yld (%) | Recrystallisation solvent |
|---|---|---|---|---|---|---|
| 85 |  | 2 | (CO₂H)₂ | 201 | 67 | Acetonitrile |

TABLE V

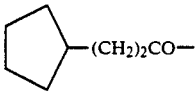

| Comp. No | R | R1 | M.p. (°C.) | Yld (%) | Analyse | Recrystallisation solvent |
|---|---|---|---|---|---|---|
| 86 | 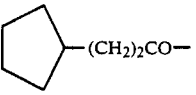 —(CH₂)₂CO— | 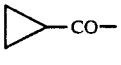 —(CH₂)₂CO— | 165 | 50 | C,H,N | Acetone |
| 87 | 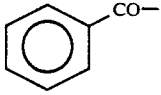 —CO— | 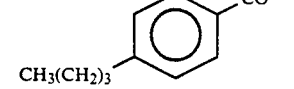 —CO— | 142 | 20 | C,H,N | Acetonitrile |
| 88 | 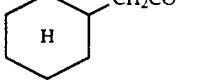 CH₃(CH₂)₃— —CO— | 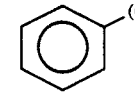 —CH₂CO— | 150 | 50 | C,H,N | Acetonitrile |
| 89 | 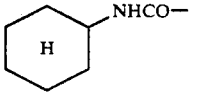 —(CH₂)₃— |  —NHCO— | 134 | 35 | C,H,N | Acetonitrile |
| 90 | 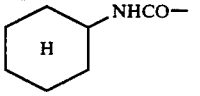 CH₃(CH₂)₃— —CO— | 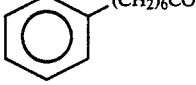 —NHCO— | 167 | 60 | C,H,N | Acetone (4) Ethyl ether (1) |
| 91 |  —(CH₂)₆CO— | 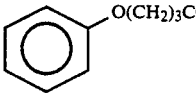 —NHCO— Cl, Cl | 102 | 25 | C,H,N,Cl | Ethyl ether |
| 92 |  —O(CH₂)₃CO— | 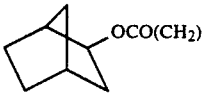 —NHCO— Cl, Cl | 124 | 30 | C,H,N,Cl | Ethyl acetate |
| 93 | 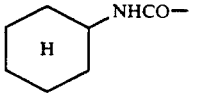 —OCO(CH₂)₂CO— | —NHCO— | 124 | 60 | C,H,N | Acetone (4) Ether (1) |

TABLE V-continued

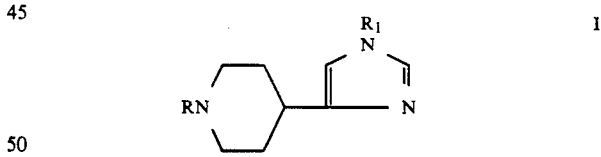

| Comp. No | R | R1 | M.p. (°C.) | Yld (%) | Analyse | Recrystallisation solvent |
|---|---|---|---|---|---|---|
| 94 | cyclopentyl-(CH$_2$)$_2$NHCO— | PhCH$_2$-CH(C$_6$H$_5$)-CH$_2$CO— | 128 | 36 | C,H,N | Ethyl acetate |

PHARMACOLOGICAL STUDY

The compounds of formula I according to the invention produce in vitro a blockade of the H$_3$ histaminergic receptors controlling cerebral histamine release and formation, and in vivo an increase in the rate of renewal of cerebral histamine, effects which establish, in particular, a psychotropic action.

The antagonism of the histamine stimulation of the central H$_3$ receptors was demonstrated by means of the method described by Arrang et al. (Nature, 1983, 302; 832-837). This method employs sections of rat cerebral cortex, and made possible the pharmacological characterisation of the H$_3$ receptors (Nature, 1987, 327; 117-123).

Exogenous histamine (at a concentration of 1 μM) produces an approximately 50% inhibition of release. This effect is progressively reversed in the presence of H$_3$ antagonists such as the compounds of the invention, added at increasing concentrations. The concentration of these compounds for which the effect of exogenous histamine is reduced by one half (IC$_{50}$) is determined, and the apparent inhibition constant (Ki) is then calculated according to Cheng and Prusoff (Biochem. Pharmacol. 1973, 22, 3099-3108), taking into account the 50% effective concentration of histamine (EC=0.1 μM). The results are collated in the following Table VI.

TABLE VI
APPARENT DISSOCIATION CONSTANTS (Ki) OF VARIOUS DERIVATIVES OF THE INVENTION AS HISTAMINE ANTAGONISTS AT RECEPTORS OF RAT BRAIN.

| COMPOUND No. | Ki (nM) |
|---|---|
| 1 | 48 |
| 8 | 63 |
| 13 | 20 |
| 20 | 59 |
| 23 | 23 |
| 38 | 84 |
| 43 | 35 |
| 48 | 65 |
| 59 | 47 |
| 60 | 120Π |
| 77 | 68 |
| 83 | 77 |
| 92 | 34 |

After intraperitoneal or oral administration to rats at a dose not exceeding 30 mg/kg, the compounds of the invention cause in vivo, an increase in the rate of renewal of cerebral histamine. The latter is estimated either by studying the decrease in the cerebral histamine level after blocking its synthesis (Garbarg et al., Europ. Jr. Pharmacol. 164, 1-11, 1989) or by studying the increase in the level of the histamine catabolite telemethylhistamine (Garbarg et al., J. Neurochem. 53, 1924-1730, 1989).

This property of being systemically active H$_3$ antagonists makes the compounds of the invention useful derivatives in human and veterinary medicine. Their therapeutic applications relate, in particular, to the central nervous system.

The present invention hence also relates to pharmaceutical compositions which contain the compounds of formula I as an active principle.

The pharmaceutical composition according to the invention may be administered to man orally, perlingually, nasally, rectally and parenterally, the active principle being combined with a suitable therapeutic excipient or vehicle.

Each single-dose preparation advantageously contains from 0.5 mg to 100 mg of active principle, it being possible for the doses which can be administered daily to vary from 0.5 mg to 200 mg of active principle.

We claim:
1. Compounds corresponding to the general formula I in which R$_1$ represents a hydrogen atom or a group —COR$_2$, in which R$_2$ represents a phenyl group, cyclopentylmethyl, cyclohexylmethyl, cyclopentylethyl or cyclohexylethyl groups or cyclopentylamino, cyclohexylamino, or phenylamino, chlorophenylamino or dichlorophenylamino groups; R represents a hydrogen atom or a group COR$_3$, in which R$_3$ represents
   (a) a linear or branched aliphatic group containing 1 to 11 carbon atoms,
   (b) a cyclane ring-system selected from the group consisting of cyclopropane, phenylcyclopropane, cyclobutane, cyclopentane, cyclohexane, cycloheptane, norbornane, adamantane, noradamantane, chlorooxonorbornane, chloroethylenedioxynorbornane, bromoethylenedioxynorbornane and the anhydride group of hydroxycarboxy-1,2,2-trimethylcyclopentanecarboxylic acid, (c) a phenyl group, unsubstituted or substituted at the para-position with a linear or branched aliphatic group containing 3 to 5 carbon atoms, or with a halogen, (d) a group $(CH_2)_m R_4$, in which m is a number between 1 and 10, and $R_4$ represents a cyclane ring system selected from the group consisting of cyclopropane, cyclobutane, cyclopentane, cyclopentane, cyclohexane, cycloheptane, norbornane, noradamantane, adamantane and 6,6-dimethylbicyclo-heptene; a phenyl group unsubstituted or monosubstituted with a fluorine atom, a chlorine atom, a methyl group or a methoxy group; a 2-thienyl or 3-thienyl group; a carboxylic acid ester group $COOR_5$ in which $R_5$ is a cyclane ring-system selected from the group consisting of cyclopropane, cyclobutane, cyclopentane, cyclohexane or norbornane; a carboxylic acid amide group of structure $CONHR_6$, in which $R_6$ represents a cyclane ring-system selected from the group consisting of cyclopropane, cyclobtuane, cyclopentane, cyclohexane or norbornane; a carboxylic acid amide group of structure

in which the group

represents pyrrolidine, piperidine or 2,6-dimethylmorpholine; or an ether group $-O-R_7$, it being possible for $R_7$ to be a phenyl group, unsubstituted or monosubstituted with a chlorine or fluorine atom or disubstituted with a chlorine atom and with a methyl group;

(e) a group $-CH=CHR_8$, in which $R_8$ represents a cyclane ring-system selected from the group consisting of cyclopropane, cyclobutane, cyclopentane, cyclohexane, norbornane or norbornene;

(f) a secondary amine group $-NH(CH_2)_n R_9$, in which n is a number between 1 and 5 and $R_9$ constitutes a cyclane ring-system selected from the group consisting of cyclopropane, cyclobutane, cyclopentane, cyclohexane or norbornane, or a phenyl group, unsubstituted, monosubstituted with a fluorine or chlorine atom or with a methoxy group or trisubstituted with methoxy groups;

R also represents a hydroxyalkenyl group

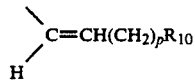

in which p is a number between 2 and 9 and $R_{10}$ represents a phenyl group or a phenoxy group; as well as a group $CSNH(CH_2)_n R_9$ in which n is a number between 1 and 5 and $R_9$ has the meaning stated above, provided that when $R_1$ represents a hydrogen atom or $R_2$ a phenyl group a cyclopentylamino, cyclohexylamino or phenylamino group, R cannot represent a hydrogen atom, $R_3$ cannot represents a phenyl group unsubstituted or substituted at the para-position by a methyl group or a halogen, a secondary amine group $-NH-(CH_2)_{1-4}-R_9$ in which $R_9$ represents a cycloalkyl (3 to 6 C), a phenyl group unsubstituted or monosubstituted with a fluorine or chlorine atom and provided that when $R_1$ represents a hydrogen atom or $R_2$ a phenyl group, a cyclopentylamino, cyclohexylamino or phenylamino group, R cannot represent a group $CSHN(CH_2)_{1-3}-R_9$ in which $R_9$ has the meaning given above.

2. Compounds according to claim 1 selected from the group consisting of
1-(hexylcarbonyl)-4-(1H-imidazol-4-yl)piperidine,
1-(cyclopropylcarbonyl)-4-(1H-imidazol-4-yl)piperidine,
1-(cyclobutylcarbonyl)-4-(1H-imidazol-4-yl)piperidine,
1-(cyclopentylcarbonyl)-4-(1H-imidazol-4-yl)piperidine,
1-(cyclohexylcarbonyl)-4-(1H-imidazol-4-yl)piperidine,
1-(cycloheptylcarbonyl)-4-(1H-imidazol-4-yl)piperidine,
1-(norbornylcarbonyl)-4-(1H-imidazol-4-yl)piperidine,
1-(norbornylmethylcarbonyl)-4-(1H-imidazol-4-yl)piperidine,
1-(norbornylpropionylcarbonyl)-4-(1H-imidazol-4-yl)piperidine,
1-(adamantylcarbonyl)-4-(1H-imidazol-4-yl)piperidine,
1-(noradamantylcarbonyl)-4-(1H-imidazol-4-yl)piperidine,
1-(chlorooxonorbornylcarbonyl)-4-(1H-imidazol-4-yl)piperidine,
1-(methylcyclopropylcarbonyl)-4-(1H-imidazol-4-yl)piperidine,
1-(phenylcyclopropylcarbonyl)-4-(1H-imidazol-4-yl)piperidine,
1-(p-butylphenylcarbonyl)-4-(1H-imidazol-4-yl)piperidine,
1-(p-t-butylphenylcarbonyl)-4-(1H-imidazol-4-yl)piperidine,
1-(3-phenylpropionyl)-4-(1H-imidazol-4-yl)piperidine,
1-(cyclohexylaminocarbonyl-n-pentanoyl)-4-(1H-imidazol-4-yl)piperidine,
1-(thiophenylpropylcarbonyl)-4-(1H-imidazol-4-yl)piperidine,
1-(1-hydroxy-4-phenyl-1-buten-1-yl)-4-(4-imidazolyl)piperidine,
1-(1-hydroxy-11-phenoxy-1-undecen-1-yl)-4-(4-imidazolyl)piperidine,
1-(cyclopentenylmethylcarbonyl)-4-(1H-imidazol-4-yl)piperidine,
1-(cyclohexylethylaminocarbonyl)-4-(1H-imidazol-4-yl)piperidine,
1-(phenylpropylaminocarbonyl)-4-(1H-imidazol-4-yl)piperidine,
1-(3-cyclopentylpropionyl)-4-[1-(3-cyclopentylpropionyl)-4-imidazolyl]piperidine,
1-(4-phenoxybutylryl)-4-[1-(2,4-dichlorophenylaminocarbonyl)-4-imidazolyl]piperidine.

3. Pharmaceutical composition containing a compound according to one of claims 1 and 2 and a therapeutically compatible excipient or vehicle.

* * * * *

UNITED STATES PATENT AND TRADEMARK OFFICE
CERTIFICATE OF CORRECTION

PATENT NO. : 5,290,790
DATED : March 1, 1994
INVENTOR(S) : ARRANG et al.

It is certified that error appears in the above-identified patent and that said Letters Patent is hereby corrected as shown below:

On title page, item [75] change "Monigue Garborg" to read as follows:

-- Monique GARBARG --

On title page, item [73] correct the spelling of the street address to read as follows:

-- Esplanade De La Paix --.

Signed and Sealed this

Sixteenth Day of August, 1994

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,290,790
DATED : March 1, 1994
INVENTOR(S) : ARRANG et al.

It is certified that error appears in the above-indentified patent and that said Letters Patent is hereby corrected as shown below:

On the title page, item [73], change "National De La Sante et De La Recherche Medicale" to read as follows:

--Institut National De La Sante et De La Recherche Medicale--.

Signed and Sealed this

Second Day of July, 1996

*Attest:*

BRUCE LEHMAN

*Attesting Officer*  *Commissioner of Patents and Trademarks*